United States Patent [19]
McGarry et al.

[11] Patent Number: 6,149,649
[45] Date of Patent: *Nov. 21, 2000

[54] RADIO FREQUENCY TRANSMYOCARDIAL REVASCULARIZATION CHANNEL FORMATION

[75] Inventors: Michael C. McGarry; W. Michael Janssen, both of Englewood, Colo.

[73] Assignee: Advanced Coronary Intervention, Englewood, Colo.

[*] Notice: This patent issued on a continued prosecution application filed under 37 CFR 1.53(d), and is subject to the twenty year patent term provisions of 35 U.S.C. 154(a)(2).

[21] Appl. No.: 08/918,018

[22] Filed: Aug. 25, 1997

[51] Int. Cl.$^7$ ........................................... A61B 18/18
[52] U.S. Cl. .............................. 606/45; 604/114; 606/49; 607/122
[58] Field of Search ........................... 606/41, 45, 48–50, 606/167, 46; 607/122; 604/113, 114

[56] References Cited

U.S. PATENT DOCUMENTS

| | | | |
|---|---|---|---|
| 5,376,087 | 12/1994 | Haber et al. | 606/27 |
| 5,403,311 | 4/1995 | Abele et al. | 606/49 |
| 5,536,267 | 7/1996 | Edwards et al. | 606/41 |
| 5,599,346 | 2/1997 | Edwards et al. | 606/41 |
| 5,605,539 | 2/1997 | Buelna et al. | 604/51 |
| 5,630,426 | 5/1997 | Eggers et al. . | |
| 5,683,366 | 11/1997 | Eggers et al. | 604/114 |
| 6,053,911 | 4/2000 | Ryan et al. | 606/33 |

*Primary Examiner*—Linda C. M. Dvorak
*Assistant Examiner*—Roy Gibson
*Attorney, Agent, or Firm*—Gibson, Dunn & Crutcher LLP

[57] ABSTRACT

A method and device for transmyocardial revascularization using RF energy. A signal probe having a signal electrode is inserted into a myocardium. A return probe having a return electrode is placed on or within the myocardium. RF energy is supplied to the signal electrode, and forms a conductive path to the return electrode. At least one fissure within the myocardium is formed along the conductive path, allowing blood to perfuse within the fissure and revascularize the myocardium. A number of probe and electrode configurations are provided, including the use of multiple probes and electrodes, hollow probes to provide a coring effect, and pressurized fluid-supplying probes.

9 Claims, 4 Drawing Sheets

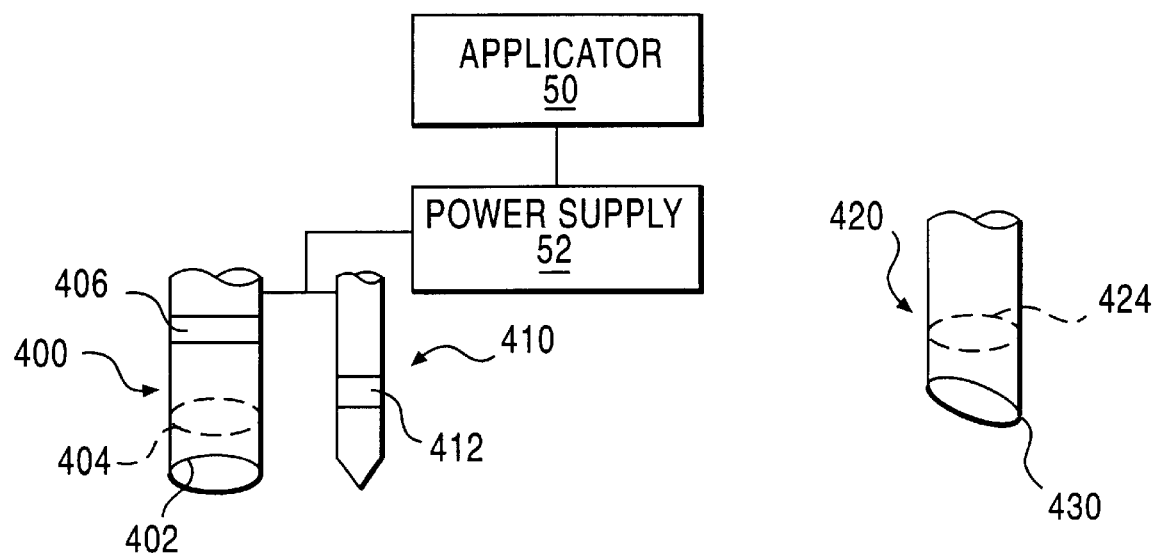
FIG.5
FIG.5A
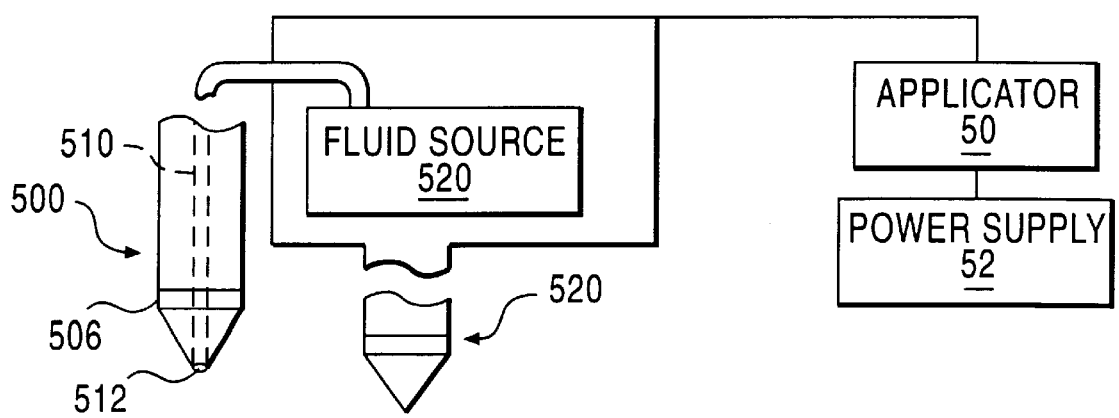
FIG.6

RADIO FREQUENCY TRANSMYOCARDIAL REVASCULARIZATION CHANNEL FORMATION

FIELD OF THE INVENTION

The present invention relates to the field of medical treatment of the heart muscle, and more particularly to using radio frequency (RF) energy to form fissures within the heart. The fissures perfuse with blood and promote angiogenesis.

BACKGROUND OF THE INVENTION

A number of treatment options exist for cardiovascular disease. These include medical treatment with drugs, various forms of intervention therapy such as balloon angioplasty, atherectomy devices, and bypass surgery. Some treatments, such as bypass or transplant surgery, are major medical procedures that entail significant risks to a patient during the surgical operation. In the case of transplants, a patient may have to wait for a prolonged period of time before another heart is available. For these and many other reasons, alternatives to major surgery are desirable. Such alternatives may be intended as comprehensive treatments or as palliative measures to sustain a patient until other treatments are available.

The present invention relates to transmyocardial revascularization (TMR). TMR is a procedure where one or more channels are made in the heart, in order to allow blood to perfuse from the ventricle into the channels and thereby relieve the effects of heart disease or coronary artery disease (CAD). As used herein, the "heart" primarily refers to the muscular tissue of that organ and specifically the ventricle, but can include any part of the organ. Such a procedure is generally described in, among other places, U.S. Pat. Nos. 5,125,924 (Rudko, 1992) and 5,125,926 (Rudko et al., 1992), which describe a pulsed laser system that purportedly overcomes problems associated with forming channels in a beating heart. Laser implemented TMR (also called laser myocardial revascularization or LMR) is also described in U.S. Pat. Nos. 5,389,096 (Aita et al., 1995) and 5,554,152 (Aita et al., 1996), which describe the use of an elongate flexible lasing apparatus to form channels within the heart. U.S. Pat. No. 5,389,096 describes creating a channel from the interior of the heart (endocardium) towards the exterior (epicardium), and stopping the channel before the epicardium is penetrated. U.S. Pat. No. 5,554,152 describes creating a channel from the epicardium through the myocardium and penetrating the endocardium. (As used herein, the "myocardium" encompasses both the epicardium and endocardium although the latter terms may be used for more specificity where appropriate).

None of the known prior art discloses TMR techniques that are not dependent upon a laser. U.S. Pat. No. 4,658,817 (Hardy, 1987) uses a combination of laser energy and mechanical penetration. While lasers may result in satisfactory TMR, they have a number of drawbacks. It is difficult to supply adequate power from external to a body, through a catheter, and to the lasing element. Shaping laser beams is difficult, if at all possible; indeed, none of the known prior art discloses a shaped channel in connection with TMR. Instead, lased channels appear to be tubular and have a constant width through the heart.

Electrosurgical devices have been developed that ablate tissue or other objects by the application of radio frequency (RF) energy. See U.S. Pat. No. 5,454,809 (Janssen, 1995). Further electrosurgical devices are disclosed in pending PCT Application No. US96/18466 titled "Medical Catheters for Ablation and Detection" of Janssen et al. While electrosurgical devices are disclosed, there is no teaching to suggest adapting such devices for TMR. The present invention overcomes limitations in TMR by providing an alternative device and method of use for forming channels within the heart.

U.S. Pat. application Ser. No. 08/777,928, commonly owned and copending herewith, describes a device and method (including several embodiments) for accomplishing transmyocardial revascularization. That application, and all other documents referred to herein, are hereby incorporated by reference.

U.S. Pat. application Ser. No. 08/882,947 titled "Applicator for Radio Frequency Transmyocardial Revascularization" describes a number of devices and methods for inserting electrodes within the myocardium. It is an object of the present invention to expand the effectiveness of that invention by creating fissures within the myocardium.

SUMMARY OF THE INVENTION

The present invention provides a device and method for revascularizing body tissue such as myocardial tissue. A signal probe is inserted within the tissue, and has one or more signal electrodes capable of supplying RF energy. A return probe is inserted within or placed on the surface tissue. The return probe has one or more return electrodes for receiving the RF energy from the signal electrodes. An RF power supply is in electrical communication with the signal and return electrodes.

The application of RF energy creates one or more fissures generally along an electrical conduction path between the signal and the return electrodes. Blood perfuses within these fissures and promotes revascularization.

Multiple probes and electrodes may be provided in a number of configurations to create a desired number and pattern of fissures.

BRIEF DESCRIPTION OF THE DRAWINGS

FIG. 5 is an elevation view of an alternative embodiment of the invention having a hollow core.

FIG. 5A is an elevation view of an alternative embodiment of the invention similar to the embodiment of FIG. 5, but having a beveled edge.

FIG. 6 is an elevation schematic view of an alternative embodiment of the invention.

DETAILED DESCRIPTION OF THE INVENTION

The present invention provides a device and method for performing radio frequency transmyocardial revascularization. One or more channels are created within the myocardial tissue of a heart. Blood perfusing within the channel is believed to provide a degree of angiogenesis, reducing the risk of subsequent heart failure and relieving angina. The present invention creates fissures that extend from a core channel that is created when a signal probe is inserted and supplied with RF energy. These fissures increase the volume of tissue that is perfused, and hence should provide comparatively greater benefits.

Figure 1:
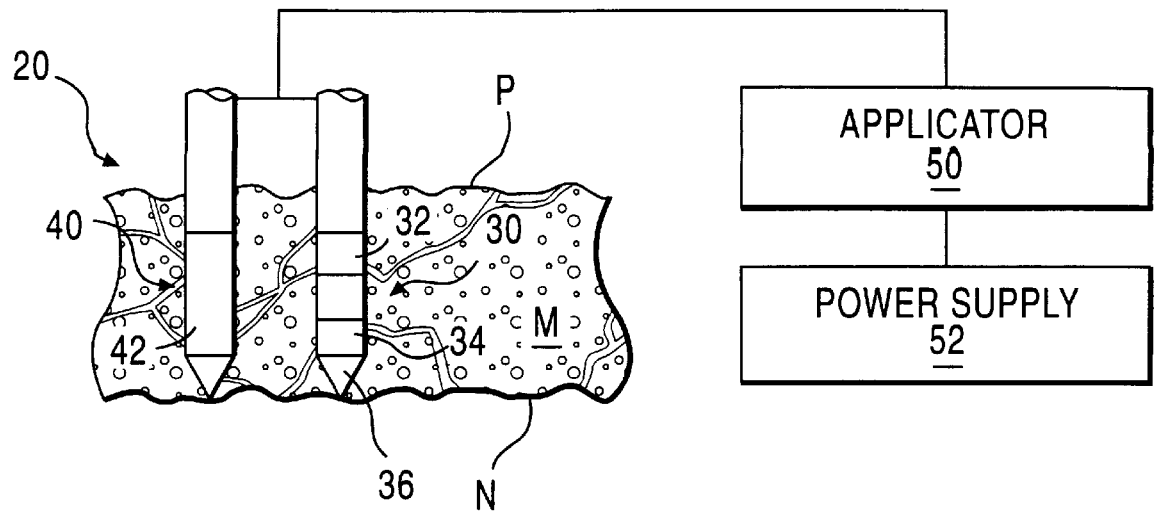
FIG. 1 is an elevation view of the device according to an embodiment of the invention, situated within tissue.

An embodiment of the invention is shown in the elevation view of FIG. 1. A number of alternative embodiments are described below, and it should be understood that the described features are to illustrate the invention and should not be construed as limitations.

A device 20 has a signal probe 30 and return probe 40 which are situated within myocardial tissue M. The signal probe 30 is preferably generally cylindrical in shape, and supports three electrodes 32, 34, and 36. The electrodes 32 and 34 are annular bands, and the electrode 36 is positioned near or at a distal tip of the signal probe 30. The return probe 40 has one electrode 42. The signal electrodes 32, 34, and 36 and the return electrode 42 are in electrical communication with a radio frequency power supply 52.

Both the signal probe 30 and return probe 40 are inserted into the myocardium M, using any applicator 50, such as according to the application "Applicator for Radio Frequency Transmyocardial Revascularization." Other applicators or application techniques may also be used. At the simplest level, the probes 30 and 40 could be inserted into the myocardium M by hand.

Figure 1A:
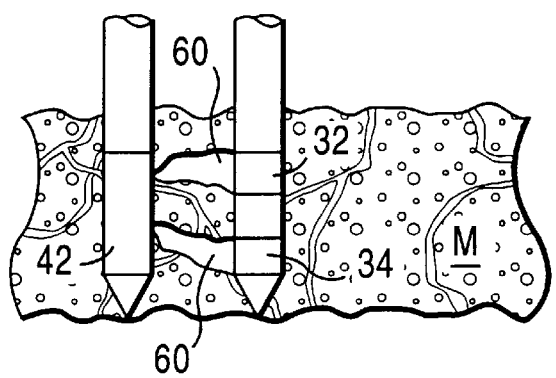
FIG. 1A is an elevation view related to the view of FIG. 1, after fissures have been created within the tissue.

The probes 30 and 40 are preferably inserted through the epicardium P until the signal probe 30 tip electrode 36 is at or about the level of the endocardium N, as shown in FIG. 1. RF energy is then supplied to the signal electrodes 32, 34, and 36. The application of RF energy to the electrodes 32, 34, and 36 causes a conductive path to be established from the signal electrodes to the return electrode 42. The RF energy applied through the myocardium creates a number of fissures 60 generally along the conducive path, as shown in FIG. 1A. Preferably, the return electrode 42 is somewhat larger than the signal electrodes so that the fissures have a greater cross section nearer the signal electrodes. While two fissures 60 are shown in FIG. 1A, one each generally along the path from electrode 32 and 34 to the return electrode 42, it is entirely possible, and usually desirable, that multiple fissures may emanate from each signal electrode. Such multiple fissures allow more surface area to receive perfusing blood within the myocardium M.

Figure 1B:
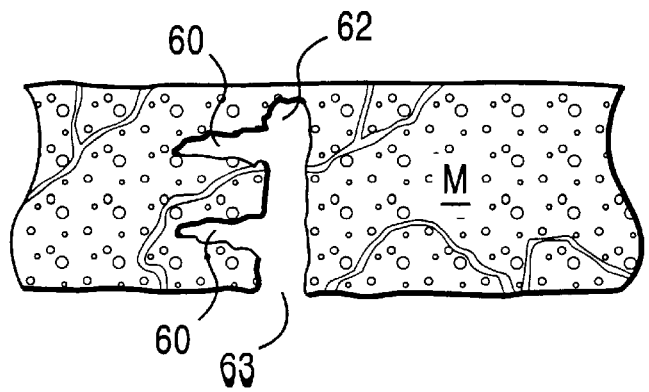
FIG. 1B is an elevation view related to FIG. 1A, after the device has been withdrawn.

The distal tip signal electrode 36 is activated to ensure that an opening 63 is created within the endocardium, as shown in FIG. 1B, showing the myocardium M after the signal probe 30 and return probe 40 have been withdrawn from the myocardium M. The opening 63 ensures that blood can perfuse from the heart ventricle through the opening 63 and a core channel 62 that is created when signal probe 30 is removed from the myocardium M. The core channel 62 results either from the physical positioning of the signal probe 30 within the myocardium M, or from the RF energy supplied by the signal electrodes, or a combination of the two. The return probe 40 can be smaller in size, if necessary, than the signal probe 30 so that a channel is not created upon removal of the return probe from the myocardium M.

The channel 62 does not extend through the epicardium P after the signal probe 30 is removed. The channel 62 may close at the epicardium P because of the natural elasticity of the myocardium M. Or, the channel can be closed by the application of pressure, suture, or other closure technique. In another closure technique, RF energy can be applied from the distal tip electrode 36 (or another electrode) to coagulate and close the channel 62.

Figure 2:
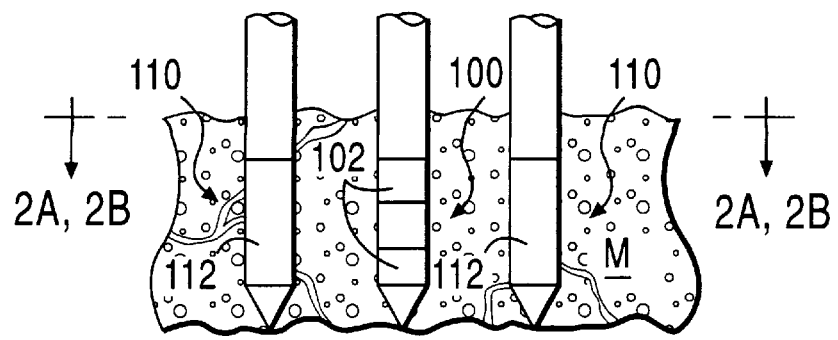
FIG. 2 is an elevation view of an alternative embodiment having multiple return probes.

Another embodiment of the invention is shown and described in connection with FIG. 2. The signal probe 100 is essentially similar to the signal probe 30, and supports a number of signal electrodes 102. Two return probes 110 are featured, each return probe having a return electrode 112. In FIG. 2, the signal probe 100 and return probes 110 are shown placed within a myocardium M. The signal probe 100 is situated between the two return probes 110. Upon application of RF electrical energy to the signal electrodes 102, fissures are formed between the signal electrodes 102 and each of the return electrodes 112. Thus, two groups of fissures (each group being between the signal probe and one of the return probes) are formed, which may be beneficial as more blood can perfuse through the myocardium M.

Figure 2A:
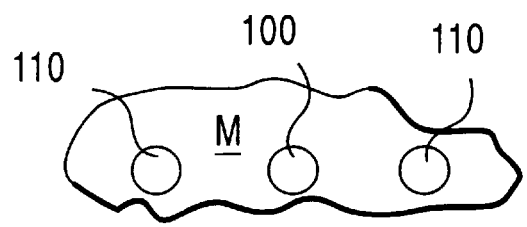
FIG. 2A is a plan view taken along the line 2A—2A of FIG. 2.
Figure 2B:
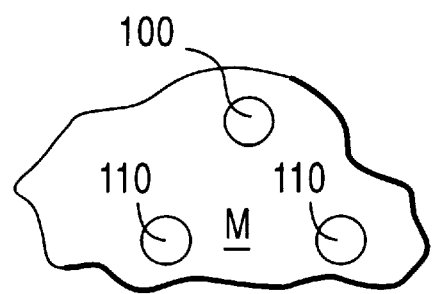
FIG. 2B is a plan view of an alternative embodiment taken along the line 2B—2B of FIG. 2.

A plan view of the signal and return probe electrode arrangement is shown in FIG. 2A. The signal probe 100 is centered between the return probes 110. An alternative arrangement is shown in the plan view of FIG. 2B. The signal probe 100 is offset from the return probes, so that the probes form the vertices of a triangle. This alternative arrangement causes the fissures between the signal probe and each of the electrodes to be offset with respect to one another, which may result in desirable healing channels.

Figure 3:
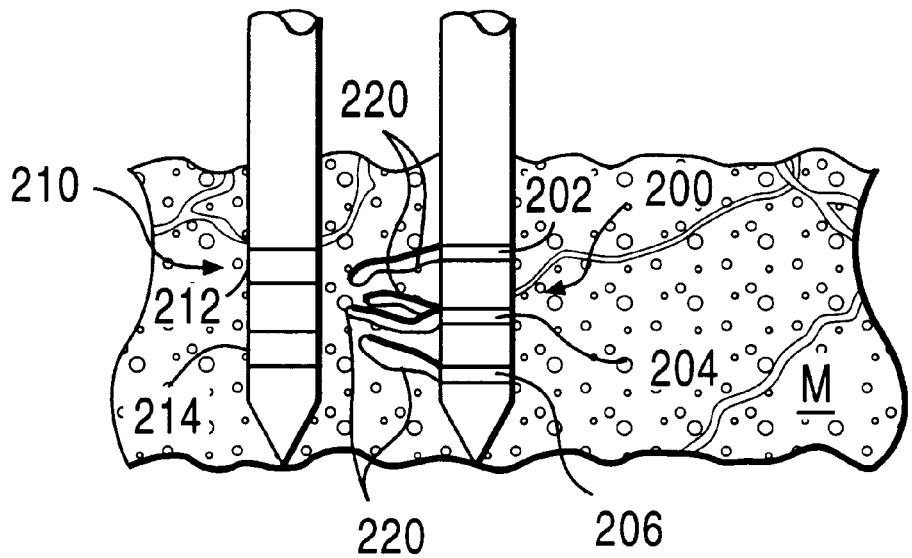
FIG. 3 is an elevation view of an alternative embodiment of the invention having multiple return and signal electrodes.

Another alternative embodiment is shown in FIG. 3. A signal probe 200 has three signal electrodes 202, 204, and 206 along its length, situated within a myocardium M. It may also have a tip electrode, not shown. A return probe 210 has two return electrodes 212 and 214. Upon application of RF energy to the signal electrodes 202, 204, and 206, a plurality of fissures 220 form between the signal electrodes and the return electrodes 212 and 214. A greater number of fissures 220 are expected to form within the myocardium M in this embodiment than in the embodiment of FIG. 1, because of the greater number of conductive paths between the signal electrodes and return electrodes.

Figure 4:
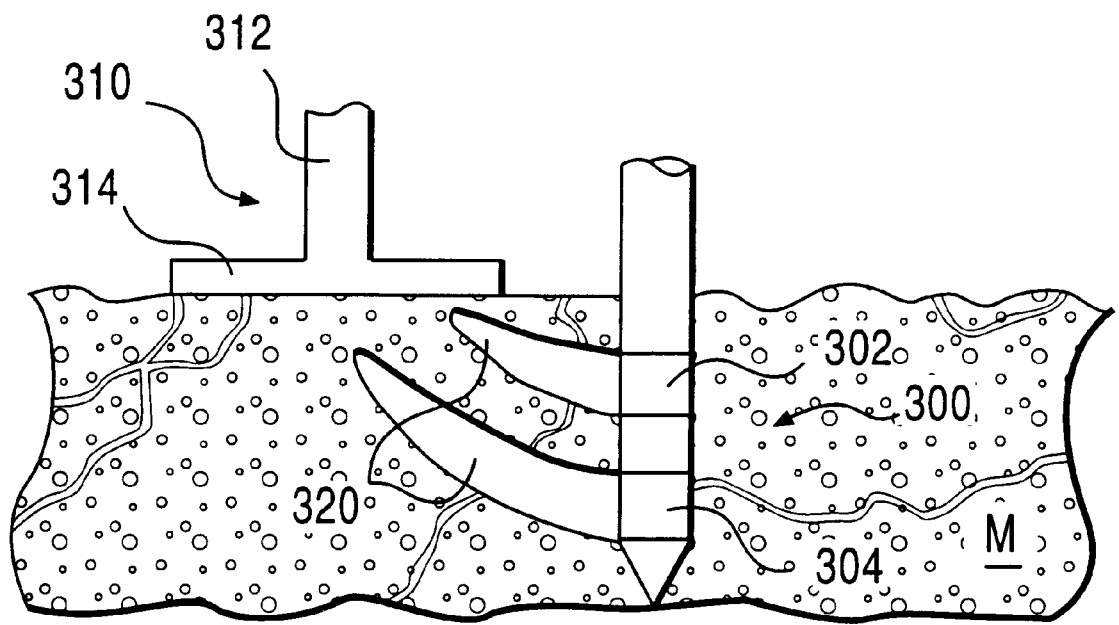
FIG. 4 is an elevation view of an alternative embodiment of the invention having a return electrode placed on the surface of the tissue.

Yet another embodiment is described in connection with FIG. 4. A signal probe 300 has signal electrodes 302 and 304 (and perhaps a tip electrode, not shown). A return probe 310 is placed on the epicardial surface P of the heart. The return probe 310 has a contact plate 314 that serves as an electrode, and is relatively larger than the area of the electrodes 302 and 304. The extending section 312 extends away from the contact plate and provides rigidity so that the plate 314 can be placed on the myocardium M. Upon an application of RF energy to the signal electrodes 302 and 304, fissures 320 are produced between the signal electrodes and the contact plate 314. This embodiment may be advantageous in that the return electrode 314 is not physically inserted into the myocardium.

Another embodiment is described in connection with FIG. 5. The embodiment has a signal probe 400, having at least one signal electrode 406. The probe 404 and electrode 406 are engaged with an applicator 50 and power supply 52 as described above. A return probe 410 having a return electrode 412 may be engaged with the applicator 50 and the power supply 52, similar to previously described embodiments.

The signal probe 400 has an opening 402 at a distal end (i.e., the end for insertion into a myocardium M), and the probe 400 is at least partially hollow so that an interior surface 404 exists within the probe 400. The hollow portion 404 is accessible from the opening 402. The significance of the opening 402 and the interior surface 404 is that insertion of the probe 400 into the myocardium M will have a coring effect so that a portion of the myocardium M will be received by the interior surface 404 as the probe is inserted, and the portion will be removed from the myocardium M as the probe 400 is withdrawn. This coring may facilitate channel formation, as a portion of the channel is formed by physically removing a portion of the myocardium M. RF energy is supplied to the electrode 406 while it is situated within the myocardium M, to complete the channel formation process.

A modification of the embodiment is shown in FIG. 5A. A signal probe 420 is substantially similar to probe 400 and engaged with like components, except that the probe 420 terminates at a beveled edge 430. The probe 420 is at least partially hollow and has an interior surface 424 accessible from the beveled edge 430. Insertion of the probe 420 has a similar coring effect as the embodiment of FIG. 5. However, the beveled edge 430 has the effect of providing a sharpened proximal end of the probe 420, so that it may be easier to physically insert the probe 420 into a myocardium M than in the embodiment of FIG. 5.

The embodiments of FIGS. 5 and 5A may optionally be used without a separate return probe. In such case, a return electrode would be positioned on the signal probe 400 (or 420), or the return could be through capacitive coupling or a patient plate as is known in the field of electrosurgical instruments.

Yet another embodiment of the invention is described in connection with FIG. 6. A signal probe 500 has at least one signal electrode 506, similar to any of the above described embodiments, engaged with an applicator 50 and a power supply 52. The probe 500 includes a lumen 510 terminating at a proximal port 512. A fluid source 520 including a suitable pump is engaged with the lumen 510 for expelling fluid through port 512. The fluid can be any liquid or gas, such as, by way of example, saline solution. Fluid can be delivered through the port 512 while the probe 500 is inserted within a myocardium M.

The fluid source 520 is capable of supplying fluid at relatively high pressure, compared to that found within a typical myocardium M. This can be accomplished by suitable selection of a pump, among other methods. The delivery of fluid, in combination with the RF power supplied to the electrode(s) 506, may enhance the channel formation process. As the channel formation takes place through the application of RF power, the pressurized fluid entering the partially formed channel inflates and enlarges the channel. It can be appreciated that the physical position of the fluid port 512 should be such that the fluid enters the partially formed channel, and may be other than as shown in FIG. 6, and should be selected in connection with the physical positioning of the electrode(s) 506. More than one fluid port 512 may be included. The essential aspect of this embodiment is that pressurized fluid assists the channel formation by applying physical pressure along with the ablative force supplied by the RF electrode.

A return probe 520 having a return electrode 522 may be engaged with the applicator 50 and power supply 52 to assist in channel formation as described above in connection with other embodiments. Alternatively, the embodiment could be used without a separate return probe, as described in connection with an optional embodiment of FIG. 5.

The method of operation of the device has been described above in connection with the embodiments, and is next summarized. The embodiment of FIG. 1 is described, it being understood that while the components differ in the other embodiments the method is essentially the same. The probes 30 and 40 are placed adjacent the myocardium M, such as through a port or other minimally invasive procedure. The probes 30 and 40 are inserted into the myocardium, and RF energy is applied to the signal electrodes 32, 34, and 36. The RF energy forms a conductive path between the signal electrodes 32, 34, and 36 and the return electrode 42, resulting in the formation of fissures. The probes are then withdrawn from the myocardium, and the core channel 62 is sealed, if necessary. The procedure may be repeated to form still more fissures, if desired.

It should be understood that various features of the above embodiments can be combined with one another, and that other embodiments may also fall within the scope of the invention. For example, the invention may include any number and configuration of signal probes and return probes, and any number and configuration of electrodes residing on the probes. The electrodes need not be physically distinct from the probe, as the probes could themselves be conductive and serve as electrodes. As further examples, any of the signal or return probes could be hollow to core out a portion of a myocardium; and any return or signal probe can have a high pressure fluid delivered to facilitate channel formation. Through the application of energy, channels and fissures are formed within the myocardium and allow perfusing blood to promote angiogenesis.

What is claimed is:

1. A device for revascularizing myocardial body tissue, comprising:

a signal probe having a distal end insertable within the tissue, the signal probe having a signal electrode situated thereon;

the signal probe being at least partially hollow and having an opening at a distal end so that an interior surface is provided, whereby insertion of the probe into myocardial tissue cores out a portion thereof; and a power supply for supplying radio frequency energy to the signal electrode and thereby to a return electrode, whereby one or more fissures are formed within the tissue generally along an electrical conduction path from the signal electrode;

wherein the distal end of said signal probe is sharpened.

2. A device according to claim 1, wherein the sharpened signal probe results from a bevel of said probe.

3. A device according to claim 1, further comprising a fluid source including a suitable pump engaged with the probe for supplying fluid through a port for assisting fissure formation.

4. A device according to claim 1, further comprising a return probe having a return electrode in electrical communication with the signal probe.

5. A device according to claim 4, wherein the return probe is insertable within the tissue.

6. A device according to claim 5, wherein the probes are generally cylindrical and are insertable within the tissue so that they are parallel.

7. A device according to claim 4, wherein the return probe is one of a plurality of return probes, whereby fissures are formed between the signal probe and return probes.

8. A device according to claim 1, wherein the signal probe is one of a plurality of signal probes.

9. A device according to claim 1, further comprising a return probe that is placed on the tissue.

* * * * *